United States Patent
Banks et al.

(10) Patent No.: US 8,781,630 B2
(45) Date of Patent: Jul. 15, 2014

(54) IMAGING PLATFORM TO PROVIDE INTEGRATED NAVIGATION CAPABILITIES FOR SURGICAL GUIDANCE

(75) Inventors: Scott Arthur Banks, Gainesville, FL (US); Frank J. Bova, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 290 days.

(21) Appl. No.: 13/124,263

(22) PCT Filed: Oct. 14, 2009

(86) PCT No.: PCT/US2009/005605
§ 371 (c)(1),
(2), (4) Date: Jul. 21, 2011

(87) PCT Pub. No.: WO2010/044852
PCT Pub. Date: Apr. 22, 2010

(65) Prior Publication Data
US 2011/0276179 A1 Nov. 10, 2011

Related U.S. Application Data

(60) Provisional application No. 61/105,324, filed on Oct. 14, 2008.

(51) Int. Cl.
G05B 15/00 (2006.01)
G05B 19/00 (2006.01)

(52) U.S. Cl.
USPC ........... 700/259; 700/258; 700/264; 600/425; 378/197

(58) Field of Classification Search
USPC .......... 700/245, 264, 258, 259; 378/4, 57, 63, 378/65, 72, 98.8, 189, 197, 198, 205; 600/102, 407, 424, 423, 414, 427, 429, 600/587; 606/130; 382/128, 131
See application file for complete search history.

(56) References Cited

U.S. PATENT DOCUMENTS

| 4,894,855 A * | 1/1990 | Kresse ........................... 378/196 |
| 6,200,024 B1 * | 3/2001 | Negrelli ......................... 378/197 |

(Continued)

OTHER PUBLICATIONS

International Application No. PCT/US2009/005605—PCT International Preliminary Report on Patentability mailed Apr. 28, 2011.

(Continued)

*Primary Examiner* — Khoi Tran
*Assistant Examiner* — Rachid Bendidi
(74) *Attorney, Agent, or Firm* — Miles & Stockbridge, P.C.; David R. Schaffer (57) ABSTRACT

An imaging platform system that provides integrated navigation capabilities for surgical guidance. The system can include two robotic arm systems, one robotic arm system holding an imaging source, and the other holding an imaging sensor. These robotic arm systems are able to move and provide three-dimensional tomographic scans, static radiographic images, and dynamic fluoroscopic image sequences. A third robotic arm system can be included in the imaging platform system as a surgeon guided tool-holder to accurately implement an image-guided surgical plan. The robotic systems can manipulate imaging and surgical components into and out of the operative field as needed, enhancing the choreography between a surgical team and assistive technology. A handle can be included as part of a manual positioning control subsystem. The handle can be mounted to an imaging robotic system above and/or below an operating table, and also can be mounted to a tool-holding robotic system.

18 Claims, 6 Drawing Sheets

(56) References Cited

U.S. PATENT DOCUMENTS

| | | | |
|---|---|---|---|
| 6,435,715 B1 * | 8/2002 | Betz et al. | 378/197 |
| 6,522,906 B1 * | 2/2003 | Salisbury et al. | 600/407 |
| 6,637,936 B2 * | 10/2003 | Crain et al. | 378/197 |
| 6,640,127 B1 | 10/2003 | Kosaka et al. | |
| 6,644,852 B2 * | 11/2003 | Crain et al. | 378/197 |
| 7,107,090 B2 * | 9/2006 | Salisbury et al. | 600/427 |
| 7,155,316 B2 * | 12/2006 | Sutherland et al. | 700/248 |
| 7,242,744 B2 * | 7/2007 | Brauss | 378/72 |
| 7,401,977 B2 * | 7/2008 | Graumann et al. | 378/205 |
| 7,441,953 B2 * | 10/2008 | Banks | 378/197 |
| 7,490,982 B2 * | 2/2009 | Gregerson et al. | 378/197 |
| 7,500,784 B2 * | 3/2009 | Grebner et al. | 378/198 |
| 7,578,618 B2 * | 8/2009 | Timmermans et al. | 378/197 |
| 7,649,620 B2 * | 1/2010 | Hessert et al. | 356/138 |
| 7,661,881 B2 * | 2/2010 | Gregerson et al. | 378/197 |
| 7,903,779 B2 * | 3/2011 | Gregerson et al. | 378/4 |
| 7,905,659 B2 * | 3/2011 | Gregerson et al. | 378/197 |
| 8,303,181 B2 * | 11/2012 | Sukovic et al. | 378/197 |
| 2003/0028091 A1 | 2/2003 | Simon et al. | |
| 2004/0106916 A1 * | 6/2004 | Quaid et al. | 606/1 |
| 2008/0118036 A1 * | 5/2008 | Jensen et al. | 378/198 |
| 2008/0130825 A1 | 6/2008 | Fu et al. | |
| 2008/0161830 A1 * | 7/2008 | Sutherland et al. | 606/130 |
| 2009/0003975 A1 * | 1/2009 | Kuduvalli et al. | 414/146 |
| 2011/0069818 A1 * | 3/2011 | Muller | 378/197 |

OTHER PUBLICATIONS

International Application No. PCT/US2009/005605—PCT International Search Report mailed May 25, 2010.

International Application No. PCT/US2009/005605—PCT Written Opinion of the International Searching Authority mailed May 25, 2010.

* cited by examiner

IMAGING PLATFORM TO PROVIDE INTEGRATED NAVIGATION CAPABILITIES FOR SURGICAL GUIDANCE

RELATED APPLICATIONS

This application claims the benefit of PCT Application No. PCT/US2009/005605, filed Oct. 14, 2009, now pending, which claims the benefit of U.S. Provisional Application No. 61/105,324, filed Oct. 14, 2008. This application corresponds to application Ser. No. 11/576,868, filed Apr. 6, 2007, now U.S. Pat. No. 7,441,953. Each patent application identified above is incorporated herein by reference in its entirety.

BACKGROUND

Over the past ten years the field of spinal surgery has undergone significant growth. From 1997 to 2003, spinal fusions have risen in ranking from among the 41 most common inpatient procedures to among the 19 most common. During this same period, image guided surgery (IGS) also has undergone significant growth. At the University of Florida (UF) Shands Teaching Hospital, in this same period, the number of spine related image guided surgical cases has increased from 25 per year to over 750 per year. Moreover, the increased use of IGS in spine surgery is not simply a function of the increased number of total surgical procedures performed. UF's 30-fold increase in IGS utilization is due primarily to the increased accuracy and flexibility provided by commercially available image guidance platforms.

In the late 1990s, the state of the art for image guidance in spine surgery was based generally on one of four paradigms: 1) Live fluoroscopic guidance, 2) Pre-surgical computed tomography (CT) scans, 3) Virtual fluoroscopy, and 4) Two-dimensional to three-dimensional (2D-3D) Registration. Live fluoroscopic guidance remains the most common intraoperative guidance approach. Spine surgeons routinely rely upon antero-posterior (AP) views to localize their entry point and lateral fluoroscopy to refine their trajectories. While effective, this technique can require the surgeon to be immediately adjacent to either the X-ray tube or image sensor, resulting in significant exposure. Recent measurements in our laboratory have equated the level of thyroid exposure from a typical three-level spine fusion to approximately 30 chest X-rays.

Pre-surgical CT scans provide high-resolution reformatted views through the surgical region of interest. While providing the best intraoperative images, the virtual image created by these scans must be registered to the patient intraoperatively. In this context, the term "register" refers to mapping reference points on the image to corresponding points on the patient's anatomy. This image-to-patient registration process is more problematic and more time consuming when applied to spine surgery than when used for cranial guidance i.e., the area where the technique was first pioneered. There is little bone available in a small volume for registration, and it is difficult to identify corresponding points in the operative field and the preoperative CT based virtual model. These technical challenges result in inaccurate registrations, and at times it is not possible to derive an acceptable model-to-patient transformation.

Virtual fluoroscopy is an attempt to overcome the drawbacks of live fluoroscopy based guidance. In this technique, one first acquires fluoroscopic views at known geometries, usually AP and lateral views. The C-arm orientation is recorded at the time of acquisition and linked to the images, permitting creation of virtual fluoroscopic views. The system then actively tracks instruments and superimposes them in a virtual fluoroscopic view. This allows simultaneous guidance on both AP and lateral images and does not require the surgeon to be in the imaging field during X-ray exposures. Superficially, this technology appears to provide the surgeon with a real advantage in personal dose reduction. Yet this technology has not gained popularity because it apparently lacks any technological advantage, does not provide unique or special views, generally requires complex image acquisition hardware, and typically requires the surgeon to hold the instrument whenever live fluoroscopic validation is required.

2D-3D Registration uses two orthogonal fluoroscopic views to register a pre-surgical CT scan. This is an attempt to provide the high quality reformatted images from pre-surgical CT scan with an easier, less invasive fluoroscopic registration process. In practice, it is often difficult to provide unambiguous planar views as required for accurate 2D-3D matching, making accurate registration problematic.

Despite all of the previously discussed drawbacks, each of these four guidance technologies provided a three-fold reduction in the rate of screws breaching the pedicle wall during placement of pedicle screws. Although this represents a significant increase in the accuracy of screw placement, the difficulties associated with system operation have severely limited system acceptance of these four guidance technologies.

Over the past three years the introduction of a fifth technology has reenergized image guided spine surgery. Intraoperative Cone-Beam CT (CB-CT) based spine IGS has provided a significant advance in overall system utility. The automatic registration of intraoperative cone beam images has provided good quality orthogonal views of the surgical trajectories while simultaneously eliminating the largest source of inaccuracy in applying pre-surgical CT images— i.e., the model-patient registration process.

Figure 1A:
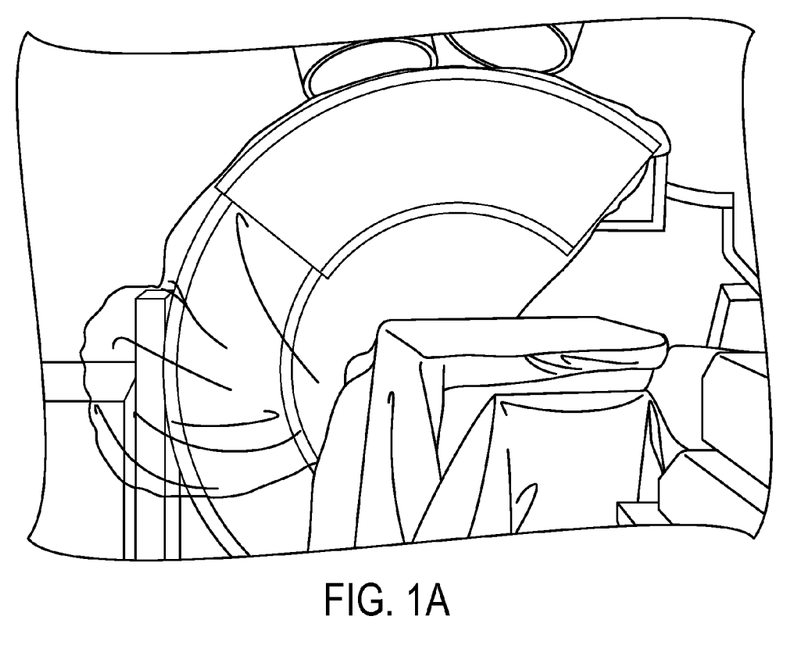
FIGS. 1a through 1c show several aspects of image guided surgery.
Figure 1B:
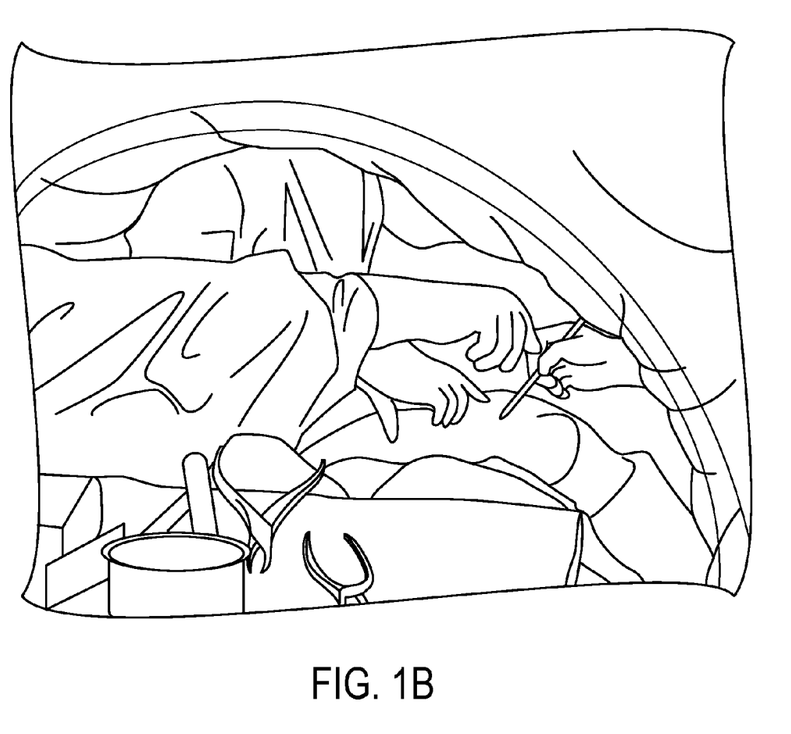
Figure 1C:
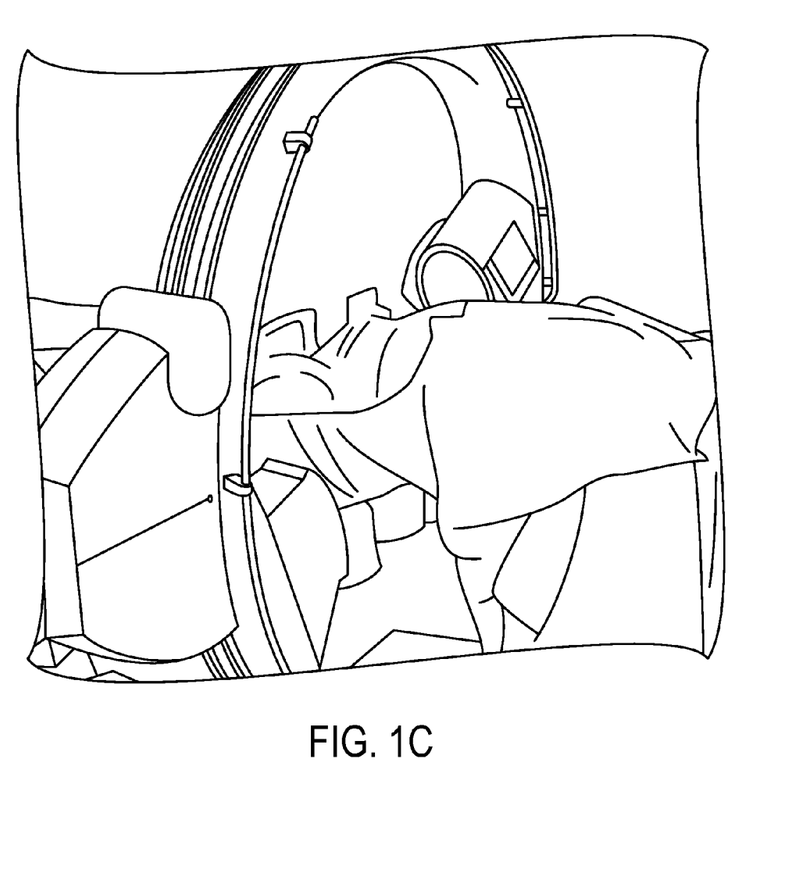

These increasingly capable guidance technologies have increased the accuracy and precision of spine surgery, but they have not decreased operative time, provided a system (including the imaging chain) which can be operated from within the surgical field, or provided intraoperative image quality comparable with diagnostic CT scanners. The complexity of the guidance system and the complicated choreography of draping the imaging chain have provided special challenges to operating room staff (see, e.g., FIGS. 1a-1c). The issues associated with surgeon access in the surgical field after the images have been obtained have also impeded wider acceptance of existing systems (see, e.g., FIG. 1b). It is also common practice for each spine instrument vendor to design unique instruments to accompany each new screw, plating, or rod system. This translates into a need for each IGS manufacturer to engineer unique mechanical adapters for each new drill, tap, and screwdriver. These unresolved technical and practical problems continue to slow acceptance of image guidance in spine surgery.

SUMMARY

The imaging platform of the present invention is aimed at overcoming the intraoperative barriers that stand in the way of IGS acceptance. The imaging platform will include a robotic imaging and tool-holding system that increases operational accuracy and precision, thereby providing higher quality imaging and reducing surgical time. The design includes three integrated robots, two for imaging, and one for tool-holding. These robotic systems can provide: 1) Advanced 2D and 3D image acquisition and reconstruction, 2) Automated image space calibration and registration, 3) Universal on-the-fly tool calibration, and 4) Advanced tool guidance. These four attributes can be integrated into an imaging platform system that provides a new level of accuracy, precision, and ease of use, resulting in decreased surgical times, while allowing significant reduction of X-ray exposure to patients and surgeons. In varying embodiments, the imaging platform will include the most useful features of current systems while eliminating engineering restraints that generally have limited system utility. The disclosed imaging platform provides significant advantage in image guidance as generally offered by intraoperative 3D imaging. While the imaging platform system can provide plain radiographic views, the system also will include intrinsic 3D guidance capabilities.

There has thus been outlined, rather broadly, the more important features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods, and systems for carrying out the several purposes of the present invention. It is important, therefore, that equivalent constructions insofar as they do not depart from the spirit and scope of the present invention, are included in the present invention.

For a better understanding of the invention, its operating advantages, and the specific objects attained by its uses, reference should be had to the accompanying drawings and descriptive matter which illustrate alternative embodiments of the invention.

DETAILED DESCRIPTION

The imaging platform system of the present invention provides integrated navigation capabilities for surgical guidance. In one embodiment, the imaging platform system includes two robotic arm systems, one robot arm system holding an X-ray source, and the other arm system holding a flat-panel X-ray image detector. These robotic arm systems will be able to move and provide three-dimensional (3D) tomographic scans, static radiographic images, and dynamic fluoroscopic image sequences. A third robotic arm system can also be included in the imaging platform system and serve as a surgeon guided tool-holder to accurately implement the image-guided surgical plan. The robotic systems can manipulate imaging and surgical components into and out of the operative field as needed, significantly enhancing the choreography between a surgical team and assistive technology, and eliminating many of the sterile-field issues associated with current intraoperative imaging systems. This imaging platform can provide several technical benefits, including: 1) All radiographic, fluoroscopic and tomographic images being automatically registered in the same coordinate space, thereby enhancing the accuracy and execution of the navigated procedure; 2) Robotic imaging permitting the use of non-equatorial scan trajectories for cone-beam tomographic reconstruction, thus providing great flexibility in the definition of scan orbits and the potential to significantly improve the quality of intraoperative tomographic reconstruction while minimizing exposures; and 3) The robotic imaging and tool-holding components providing enhanced operative functionality, while being able to quickly retract from the operative field when not needed to enhance the operative choreography.

Figure 2:
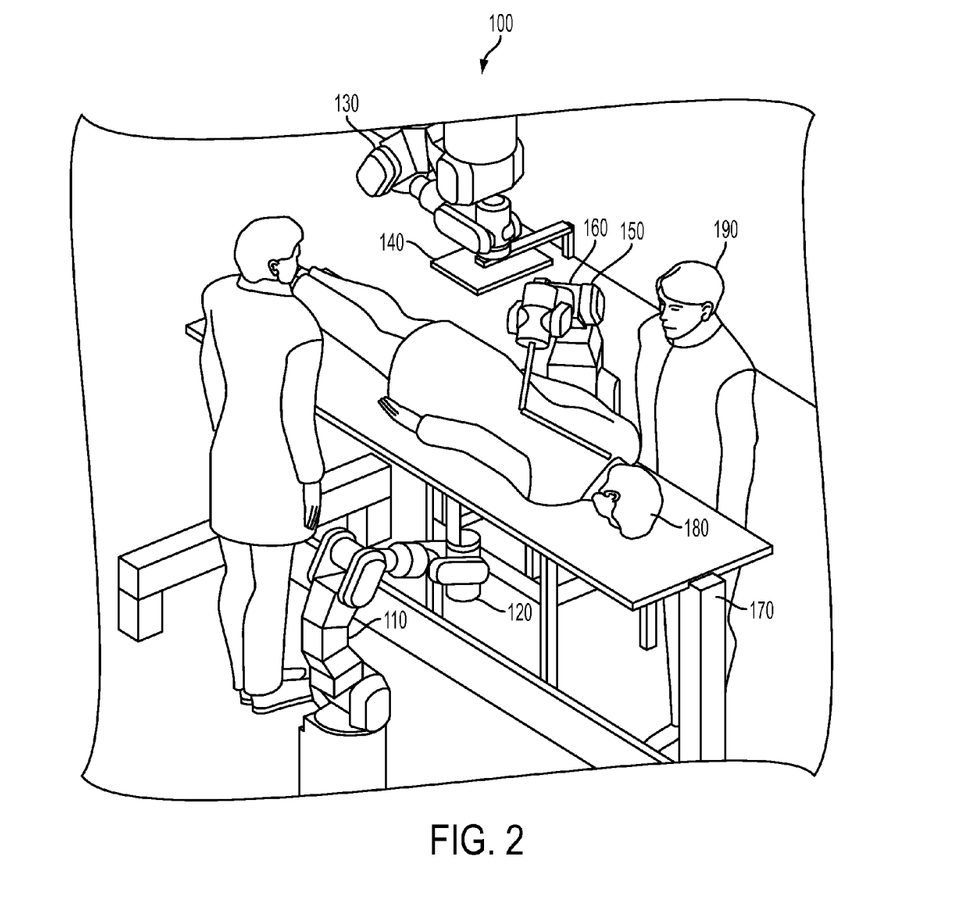
FIG. 2 shows an embodiment of the invention with a three-robot configuration to provide intraoperative imaging and surgical tool-holding capabilities in accordance with the present invention.

FIG. 2 shows an embodiment of the imaging platform system [100] with a three-robot configuration to provide intraoperative imaging and surgical tool-holding capabilities in accordance with the present invention. As shown in FIG. 2, a first robotic arm system [110] holds an X-ray source [120], positioned below an operating table [170] on which a surgical patient [180] is positioned. A second robotic arm system [130] holds an X-ray image detector [140], positioned above the operating table [170]. These robotic arm systems are able to move and provide 3D tomographic scans, static radiographic images, and dynamic fluoroscopic image sequences. A third robotic arm system [150] holds a surgical tool [160], positioned above the operating table [170]. A surgeon [190] may guide the tool held in the robotic arm, to accurately implement, for example, an image-guided surgical plan.

An embodiment of the imaging platform system includes three subsystems or components: Manual Positioning Control, Automatic Scans, and an integrated Tool-Holding Robot.

Figure 3:
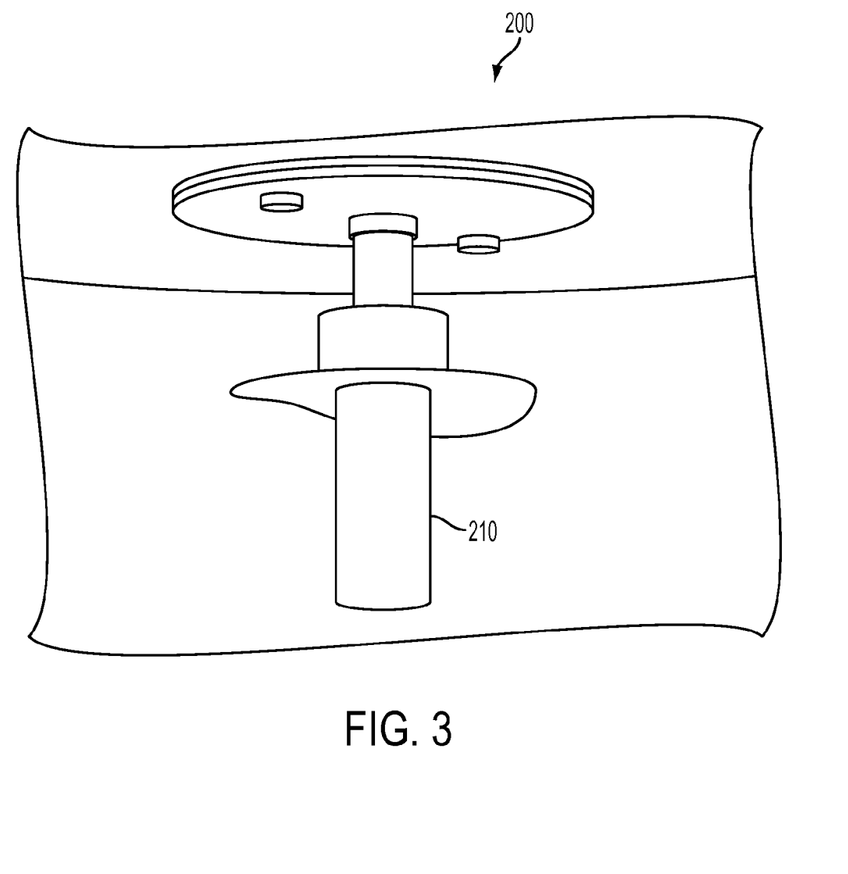
FIG. 3 shows an exemplary embodiment of a portion of a manual positioning control subsystem in accordance with the present invention.

Manual Positioning Control—One aspect of the imaging platform system is a manual positioning control subsystem that provides a surgeon the ability to easily and intuitively control the technology associated with image-guided procedures. Interaction with the imaging and tool-holding robots needs to be as easy as adjusting an overhead surgery light. At the same time, these mobile instruments need to safely navigate the complex spatial environment surrounding the patient. FIG. 3 shows an exemplary embodiment of a portion of the manual positioning control subsystem [200]. As shown in FIG. 3, a handle is mounted to a portion of the manual positioning control subsystem [200]. The handle [210] can be mounted to an above-the-table imaging robotic system and/or to a below-the-table imaging robotic system. Alternatively, the handle can be mounted to a tool-holding robotic system. A master-slave model can be used to control a below-the-table X-ray source robot and an above-the-table sensor or detector robot. A handle on the above-the-table sensor robot can be grasped by the surgeon and moved into position for the desired radiographic projection. The below-the-table x-ray source robot will move accordingly to maintain source-sensor alignment and distance. This motion can be augmented by a collision avoidance routine, pre-oriented with a Jackson Table or other suitable operating table, for example, and other environmental obstacles, which will reflect a force field back to the surgeon's handle. The surgeon will feel a 'virtual wall' in the direction approaching an obstacle, but will maintain free motion along obstacle-free trajectories. This simple means of interaction will give the surgeon direct and intuitive control of the guidance technology. A similar control mode can be utilized for the surgical tool positioning robot, without the need for a master-slave configuration. In alternative embodiments, the manual positioning control subsystem can also comprise: a quick routine for registering an operating table, robots, and other equipment; a control panel for allowing the surgeon to control the mode and functionality of the robots; and a controller that is tuned for comfortable manual interaction with the robots.

Spatial positioning of the robotic systems and other equipment in the operating room can be accomplished using two approaches—traditional electromagnetic or optical tracking technology and a robot-intrinsic calibration approach. The robot intrinsic approach will utilize standard X-ray calibration targets attached to the sensor robot and tool-holder robot to identify the spatial pose of each robot with respect to the source robot—with the computed source-sensor or source-tool-holder pose and the geometry/stiffness calibrated robot model, it is straightforward to compute the pose of each robot's base reference frame with respect to the source robot's base reference frame. The accuracy of this intrinsic calibration approach can be compared in reference to ground-truth systems (e.g., using traditional electromagnetic or optical tracking technology), and also by back projection of the calibration objects and computation of residual measurement errors. Once the robots' locations are known, they can be used easily to sweep 'free-fly zones' or to probe fiducials on the Jackson table, for example, and other obstacles within the peri-surgical field to develop a 'world-model' for obstacle avoidance. A generic model of a Jackson Table and head holder can be created so that it can be localized with respect to the robots by probing two or three fiducial points. A similar approach can be used for other common equipment in the peri-surgical field.

Figure 4:
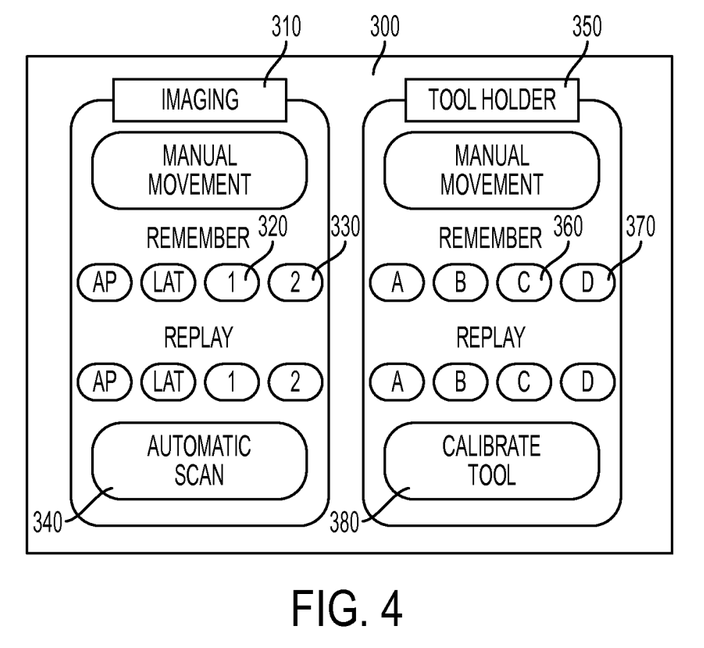
FIG. 4 shows an exemplary embodiment of a system control interface in accordance with the present invention.

Another aspect of the imaging platform system is the ability to give the surgeon direct and easy control of the imaging and surgical robotic tools. A simple command interface will be provided to the surgeon as part of the manual positioning control subsystem. The interface can include a push-button interface box as shown in FIG. 4 and described below. This interface will enable different robotic functions and can be sized so that it is easily covered with a sterile plastic bag.

An impedance control strategy can be used to enable easy manual movement of the robotic systems with intrinsic collision avoidance. Impedance control is one approach to providing highly tunable force control to robots based on modeling the force interaction as a parallel spring and dashpot: $F_{imp} = k_1(\bar{x} - \bar{x}_d) + k_2(\dot{\bar{x}} - \dot{\bar{x}}_d)$ where $k_1$ corresponds to a spring stiffness and $k_2$ a damping coefficient, and $\bar{x}$, $\bar{x}_d$, $\dot{\bar{x}}$, and $\dot{\bar{x}}_d$ correspond to the current and desired end-effector positions and velocities. The impedance parameters $k_1$ and $k_2$ can be adjusted dynamically to create a virtual wall to the surgeon when one or more of the robotic systems nears an obstacle. The impedance parameters can include a fixed component that is tuned for comfortable free motion of the robots. A dynamic component for each impedance parameter can be computed to provide exponentially increased stiffness or damping as any part of the robots or payloads approaches an environmental obstacle. Impedance controllers providing maximum dynamic performance can be implemented and tuned for surgeon/robot interaction.

Automatic Scans—One distinction and advantage the imaging platform system of the current invention will have over conventional C-arm or closed-ring based systems for cone-beam computed tomography is the ability to move in non-equatorial scanning trajectories. This spatial flexibility provides the opportunity to develop novel scan trajectories and avoid the pitfalls of equatorial scans in the operative context (e.g., lateral projections, sterile field, limited reconstruction volumes, and obtrusive devices). Implementing this system capability for relatively free-form scan geometries follows directly from the imaging platform system manual positioning capabilities previously described. A surgeon can manually position the above-the-table sensor robot to focus at the proximal and distal extents of the anatomic region for reconstruction. FIG. 4 shows an exemplary embodiment of an imaging system control interface in accordance with the present invention. While embodiments of the current invention are not intended to be held to any particular mechanism, it is envisioned that a surgeon will use the control interface to, for example, press 'Remember' buttons 1 and 2 [320, 330] on the Imaging portion [310] of the control panel [300] as shown in FIG. 4. Based on spatial registration of the imaging robots, the patient, the table, and other obstacles, an appropriate obstacle-free scan trajectory can then be computed and executed upon pressing the 'Automatic Scan' button [340] on the control panel [300] as shown in FIG. 4. Executing the scan necessarily prioritizes safety, positioning accuracy and scan speed. Scan safety is insured through the environment registration and obstacle avoidance previously discussed, as well as through a visual display for the surgeon showing the computed scan trajectory. In addition, bump sensors with micro-switches can be installed on the source and sensor payloads to freeze robotic motion should contact occur with an object that is not part of the environmental model.

Scan speed and accuracy will be a function of robot capabilities and the control system. An example of implementation of the system includes a pair of PA10-6C robots. Three different control strategies can be implemented. First, a model-based controller accounting for joint flexibilities and payload inertial properties can be implemented. This controller will rely only on feedback from the robot joint encoders. Second, the model-based controller can be augmented with an Extended Kalman Filter observer, for example, incorporating pose feedback from source and sensor mounted electromagnetic trackers. Finally, the controller can be augmented with force-torque feedback from each robot's end effector. The first controller can provide extremely accurate end-point position control, but the augmented controllers can be used, for example, to improve the dynamic tracking performance of the system.

Tool-Holder Robot—An often frustrating element of image-guided surgical procedures is the requirement for a surgeon to hold a tool in a fixed position while determining its proper alignment with regard to some ideal trajectory. Ideally, the surgeon would be able to place the tool where desired, and have it fixed in that position unaided while the surgeon verifies alignment. This can be a relatively simple task for a robotic arm of the imaging platform system, and builds directly from the manual interaction capability described for the imaging robots. The tool-holding robot could move freely—subject to collision avoidance—as guided, and remain in a fixed position when released by the surgeon. The tool-holding robotic capability will build upon the capabilities for manual interaction with the imaging robots. An example of implementation of this system includes a PA10-6C robot.

The tool-holder robotic system will be compatible with the widest possible range of tools or instruments, as surgeons often are frustrated when their image guided system is not capable of registering or utilizing the hand tools available in the operating room. Thus, a universal holder/clamp that is compatible with the tools most often required for image-guided spinal surgery (e.g., trochars, drills, taps, and screwdrivers) can be attached to the end of the tool-holding robot. FIG. 4 shows an exemplary embodiment of a tool-holder system control interface in accordance with the present invention. While embodiments of the current invention are not intended to be held to any particular mechanism, it is envisioned that a surgeon will use the control interface to, for example, press 'Remember' buttons C and D [360, 370] on the Tool Holder portion [350] of the control panel [300] as shown in FIG. 4. Based on spatial orientation of the tool-holding robots, the patient, the table, and other obstacles, an appropriate tool calibration can then be performed upon pressing the 'Calibrate Tool' button [380] on the control panel [300] as shown in FIG. 4.

Additionally, the tool-holder robotic system will allow for any tool or instrument to be registered conveniently for use with image guidance. A procedure to quickly register any tool tip with the robot can be implemented. An exemplary implementation of a procedure for registering a new tool is as follows. A sterile target can be fixed at a convenient or predetermined location in the surgical field and registered using either optical, electromagnetic (EM) or robot probes. The new tool or instrument is attached to the universal tool holder/ clamp and the tool tip is placed in a small detent or recess in the target. The tool is moved in a conical arc while the motion is recorded through the robotic arm—and an EM or optical tracker—, and the endpoint can be accurately computed with respect to the robot and navigation reference frames.

An exemplary embodiment of the imaging platform system is structured around a surgical workflow, providing a surgeon with what is needed when it is needed. An example of how an embodiment of the imaging platform system will be implemented addresses the first problem that often is encountered as the surgeon begins a spine procedure; i.e., the current design of an intraoperative radiographic device does not include the ability to take an extended cephalic-caudal view, as is routinely available as a scout view from CT and magnetic resonance (MR) imaging. Without this capability the surgeon is forced to take multiple radiographs, beginning at a known endpoint on the spine, such as the C2 vertebra, and counting until the correct vertebral body is unambiguously identified. This could require several radiographs and moving the fluoroscopic unit several times. During this process, the surgeon often finds it necessary to hold a clamp in the radiographic field to help establish a surface point on the skin to correlate with the radiographic image. An embodiment of the imaging platform system will remedy this situation, allowing the surgeon to take hold of a handle on an above-table imaging receptor and, in a non-radiographic mode, designate the beginning and ending points of the desired AP radiograph. A robotic system can then retrace that path, obtaining a contiguous X-ray image and display the entire scan on a computer screen. The surgeon will then be provided the full radiograph upon which he or she can designate the desired surgical levels. A third robotic system, designated for tool holding, can hold a marker in place over the designated vertebral body while a confirmatory radiograph is obtained. This same robotic control of the imaging chain will allow similar extended 3D imaging of all regions of interest, allowing intraoperative scans, for example, from the occiput to the coccyx. It is the robotic linkage of an X-ray source and an X-ray detector spatially tied to a robot dedicated to tool holding that will enable this new design to overcome pervious barriers.

Full spatial control for both the detector and X-ray source robots enables the system to perform unlimited imaging trajectories, including full 360° cone beam data acquisition, partial cone-beam image acquisition, tomosynthesis, and coded aperture tomography. Scan trajectories that do not require equatorial orbits around the patient could be particularly beneficial, i.e., they would eliminate intraoperative problems associated with maintaining a sterile field. For example, if data acquisition is limited to ±60° arcs, the X-ray tube would not need to be raised into or above the lower extent of the sterile field. This would significantly reduce the draping currently required with any of the commercial intraoperative cone beam products. The imaging platform robotic system would only require a simple sterile drape over the image detector.

The ability to individually move components of the imaging platform system can also eliminate the issues associated with an imaging system being in a surgeon's way. Some systems have attempted to address this problem by providing a move-and-return function, but the distance systems' ability to move out of the surgeon's way often is limited by the proximity of anesthesia equipment. One often finds that movement of cone beam systems away from the operative site actually moves the imaging system between the optical tracker's line of sight and the operative site, interfering with patient and tool tracking. The robotic imaging approach of the imaging platform system not only eliminates the structure that mechanically ties the X-ray source to the image acquisition system but also allows the system to be easily translated or elevated for easier access to the surgical site. Accurate robotic tracking provided by the imaging platform system removes the need for either optical or electromagnetic tracking of the image chain and surgical tools. All that would be required is a single reference for dynamic tracking to account for patient movement relative to the robot frame of reference; this also could be tracked using suitable mechanical means.

In state of the art image guidance systems a surgeon, or their designee, typically has two primary types of interaction with the IGS system during a case. The first is to provide setup information concerning the tools to be tracked. The second is to advance the system between image acquisition screens and image guidance screens. Using the imaging platform robotic system and its automatic on-the-fly tool registration capability, the only required interaction will be to advance the system between image acquisition and guidance. This reduced set of tasks can easily be controlled through a limited button keypad, such as that shown in FIG. 4. This keypad easily can be draped and kept within the sterile field. The imaging platform system will include a sterile force-sensing handle on the image sensor robot, such as that previously described and shown in FIG. 3. Such a handle might be similar to that used on an overhead operating light, and can allow the system to be controlled by a single individual operating from within the surgical field.

The coordination of the three robotic systems will also provide the surgeon with more versatile tool guidance. It is common for IGS systems to only track an instrument. The robotic control of the instrument provided by the imaging platform system will enable the surgeon to be softly guided down a trajectory using haptic or force feedback, whereby actuators apply forces to the surgeon for touch feedback. Once the surgeon is satisfied with a trajectory, tool movement can be restrained to only move along that desired or approved trajectory. The tool also can be made to stay fixed in space whenever the surgeon releases their grip. These system features can extend image guidance from a simple tracking technology to providing valuable surgical assistance throughout a surgical procedure.

The entire disclosures and contents of each reference, patent and patent application referred to above are expressly incorporated herein by reference. Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, since numerous modifications will readily occur to those skilled in the art, it is not desired to limit the invention to the exact construction and operation illustrated and described, and accordingly, all suitable modifications and equivalents may be resorted to, falling within the scope of the invention.

What is claimed is:

1. An imaging platform system comprising:
    an imaging system, the imaging system further comprising a robotic imaging source and a robotic imaging sensor, the robotic imaging source comprising an X-ray source mounted to a first robotic arm, the robotic imaging sensor comprising a flat-panel X-ray image detector mounted to a second robotic arm;
    a tool-holding system, the tool-holding system further comprising a robotic tool-holder with a third robotic arm; and
    a control system coupled to the imaging system and the tool-holding system and configured to control motion of the first through third robotic arms, the control system further comprising a haptic interface and a control panel;
    wherein the imaging system and the tool-holding system are integrated and are adapted to provide integrated navigational capabilities for surgical guidance,
    one of the X-ray source and the X-ray image detector is configured for manual positioning by a user and has a first handle attached thereto,
    the control system is further configured to monitor said manual positioning and to control the first and second robotic arms based thereon, and
    the control system is configured to execute a scan trajectory automatically by controlling movement of the first and second robotic arms based on information from said manual positioning by the user.

2. The imaging platform system of claim 1, wherein one of the robotic imaging source and the robotic imaging sensor is adapted to be positioned below an operating table.

3. The imaging platform system of claim 1, wherein the robotic tool-holder of the tool-holding system is adapted to be positioned above an operating table.

4. The imaging platform system of claim 1, wherein the control system is configured to control the first and second robotic arms using a master-slave relationship such that a movement of said one of the X-ray source and the X-ray image detector yields a mirrored displacement of the other of the X-ray source and the X-ray image detector.

5. The imaging platform system of claim 1, wherein the control system haptic interface further comprises a second handle attached to the tool-holding system for manually controlling the tool-holding system.

6. The imaging platform system of claim 1, wherein the control system further comprises a force-torque feedback that restrains manual positioning by the user of the robotic imaging source or the robotic imaging sensor.

7. The imaging platform system of claim 1, wherein the system is adapted to hold a surgical tool and to restrain manual positioning by the user of the tool to a desired trajectory.

8. The imaging platform system of claim 1, wherein portions of the imaging system and the tool-holding system are adapted to move into and out of an operative field to enhance operative choreography.

9. The imaging platform system of claim 1, wherein the imaging system is adapted to provide 3D tomographic scans, static radiographic images, and dynamic fluoroscopic image sequences.

10. The imaging platform system of claim 1, wherein the imaging platform system is adapted to move in non-equatorial scanning trajectories.

11. A method of generating a scout view image for an image-guided surgical procedure, the method comprising:
    (a) in a non-radiographic imaging mode, manually positioning one of an X-ray source and an X-ray sensor mounted on a first robotic arm so as to designate a beginning point of a desired anteroposterior (AP) radiograph, the other of the X-ray source and the X-ray sensor being mounted on a second robotic arm;
    (b) in the non-radiographic imaging mode, manually positioning said one of the X-ray source and the X-ray sensor mounted on the first robotic arm so as to designate an ending point of the desired AP radiograph;
    (c) receiving at a control system the designated beginning point and the designated end point;
    (d) by the control system, calculating respective radiographic imaging paths for the X-ray source and the X-ray sensor;
    (e) by the control system, controlling the first and second robotic arms to follow the calculated radiographic imaging paths from the designated beginning point to the designated end point while imaging using the X-ray source and the X-ray sensor;
    (f) by the control system, generating a contiguous X-ray image scan based on signals from the X-ray sensor obtained during (e);
    (g) by the control system, displaying the X-ray image scan on a computer screen;
    (h) manually positioning a marker mounted on a third robotic arm to designate a spatial point; and
    (i) by the control system, while controlling the third robotic arm to hold the marker in place at the spatial point, repeating (e) so as to generate a confirmatory radiograph.

12. A method of registering a tool for use with an image platform system, the image platform system including an X-ray source mounted on a first robotic arm and an X-ray sensor mounted on a second robotic arm, the image platform system further including a robotic tool-holder with a third robotic arm, the method comprising:
    (a) fixing a sterile target at a location in a surgical field navigation reference frame of the image platform system, the sterile target including a small detent or recess for tool registration;
    (b) registering the sterile target using optical, electromagnetic (EM), or robot probes;
    (c) attaching the tool to the robotic tool-holder;
    (d) moving the third robotic arm such that a tip of the attached tool is positioned within said small detent or recess of the sterile target;
    (e) moving the attached tool in a conical arc;
    (f) at a same time as the moving in (e), by a control system, recording the motion of the attached tool through the third robotic arm; and
    (g) by the control system, calculating the tip of the attached tool with respect to the third robotic arm and the navigation reference frame based on the recorded motion.

13. The imaging platform system of claim 1, wherein:
said manual positioning by the user comprises designating a start point and an end point for a desired imaging scan, and the control system is configured to calculate the scan trajectory for the desired image scan based on the designated start and end points and to control the first and second robotic arms to follow the calculated scan trajectory.

14. The imaging platform system of claim 1, wherein:
said manual positioning by the user comprises moving said one of the X-ray source and the X-ray image detector along a desired scan path, and the control system is configured to store the scan path as the desired scan trajectory and to control the first and second robotic arms to subsequently follow the scan trajectory.

15. The imaging platform system of claim 1, wherein:
said manual positioning by the user comprises moving said one of the X-ray source and the X-ray image detector along a desired path, and the control system is configured to provide feedback via the haptic interface that is indicative of an obstruction in a mirrored path of the other of the X-ray source and the X-ray image detector.

16. The imaging platform system of claim 1, wherein the control system is configured to record the manual positioning to define the scan trajectory for subsequent automatic movement of the first and second robotic arms during a desired radiographic scan.

17. The imaging platform system of claim 1, wherein the control system is configured to provide feedback to the tool holder during manual positioning thereof by a user, the feedback being indicative of a desired position for the tool.

18. The method of claim 11, further comprising, during one of the manual positionings of (a) and (b), by the control system, providing a haptic feedback response via the first robotic arm that is indicative of a blockage in a mirrored pathway of the second robotic arm.

\* \* \* \* \*